United States Patent
Neijzen et al.

(10) Patent No.: US 9,964,487 B2
(45) Date of Patent: May 8, 2018

(54) DETECTION APPARATUS FOR DETECTING PARTICLES

(71) Applicant: KONINKLIJKE PHILIPS N.V., Eindhoven (NL)

(72) Inventors: Jacobus Hermanus Maria Neijzen, Eindhoven (NL); Johannes Joseph Hubertina Barbara Schleipen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days. days.

(21) Appl. No.: 15/106,856

(22) PCT Filed: Dec. 10, 2014

(86) PCT No.: PCT/EP2014/077119
§ 371 (c)(1),
(2) Date: Jun. 21, 2016

(87) PCT Pub. No.: WO2015/096981
PCT Pub. Date: Jul. 2, 2015

(65) Prior Publication Data
US 2017/0003222 A1  Jan. 5, 2017

(30) Foreign Application Priority Data
Dec. 23, 2013  (EP) ..................... 13199275

(51) Int. Cl.
*G02B 21/18*   (2006.01)
*G01N 15/00*   (2006.01)
(Continued)

(52) U.S. Cl.
CPC ....... *G01N 21/552* (2013.01); *G01N 15/1436* (2013.01); *G01N 21/27* (2013.01);
(Continued)

(58) Field of Classification Search
None
See application file for complete search history.

(56) References Cited

U.S. PATENT DOCUMENTS 4,489,239 A * 12/1984 Grant ..................... G01N 21/39
                                                    250/338.5
5,637,458 A *  6/1997 Frankel .................. B01J 19/004
                                                    356/244
(Continued)

FOREIGN PATENT DOCUMENTS

JP    11264935 A    3/1999
JP    200858249 A   3/2008
(Continued)

*Primary Examiner* — Tri Ton
*Assistant Examiner* — Jarreas C Underwood

(57) ABSTRACT

The invention relates to a detection apparatus (1) for detecting particles on or close to a particles detection surface (5) in a first optical detection mode and in a second optical detection mode, wherein a component of a light detection system (8) and/or a component of an optical system (9) of the detection apparatus is arranged to be used in the first detection mode and in the second detection mode. Since a component of the light detection system and/or a component of the optical system is arranged to be used in the first detection mode and in the second detection mode, this component does not need to be provided twice, i.e. for being used in the first detection mode and for being used in the second detection mode. This can lead to a reduced number of components and can make the detection apparatus technically less complex.

15 Claims, 8 Drawing Sheets

(51) Int. Cl.
   *G01N 21/00*   (2006.01)
   *G01N 21/552*  (2014.01)
   *G01N 21/27*   (2006.01)
   *G01N 15/14*       (2006.01)

(52) U.S. Cl.
   CPC ..... *G02B 21/18* (2013.01); *G01N 2015/1452* (2013.01); *G01N 2201/06* (2013.01)

(56) References Cited

U.S. PATENT DOCUMENTS

| | | | |
|---|---|---|---|
| 6,280,960 B1* | 8/2001 | Carr | G01N 15/1463 356/244 |
| 7,333,198 B1* | 2/2008 | Liphardt | G01N 21/21 356/364 |
| 7,399,600 B2* | 7/2008 | Carr | G01N 15/02 356/317 |
| 8,797,028 B2* | 8/2014 | Verschuren | G01N 15/06 324/244 |
| 9,268,121 B2* | 2/2016 | Van Den Eerenbeemd | G01N 21/552 |
| 9,339,813 B2* | 5/2016 | Kahlman | B01L 3/5027 |
| 2002/0045276 A1* | 4/2002 | Yguerabide | C12Q 1/6816 436/518 |
| 2003/0007896 A1* | 1/2003 | Tiefenthaler | G01N 21/552 422/91 |
| 2012/0184048 A1* | 7/2012 | Van Ommering | G01N 33/54313 436/164 |
| 2012/0202194 A1* | 8/2012 | Evers | G01N 15/0612 435/5 |
| 2013/0114076 A1* | 5/2013 | Schleipen | A61B 5/0059 356/246 |

FOREIGN PATENT DOCUMENTS

| | | |
|---|---|---|
| JP | 2008096296 A | 4/2008 |
| WO | 2008072156 A2 | 6/2008 |
| WO | 2011036634 A1 | 3/2011 |
| WO | 2011036638 A1 | 3/2011 |
| WO | 2012073178 A2 | 6/2012 |
| WO | 2013001431 A1 | 1/2013 |
| WO | 2013035009 A1 | 3/2013 |

* cited by examiner

000# DETECTION APPARATUS FOR DETECTING PARTICLES

CROSS-REFERENCE TO PRIOR APPLICATIONS

This application is the U.S. National Phase application under 35 U.S.C. §371 of International Application No. PCT/EP2014/077119, filed on Oct. 10, 2014, which claims the benefit of European Patent Application No. 13199275.2, filed on Dec. 23, 2013. These applications are hereby incorporated by reference herein.

FIELD OF THE INVENTION

The invention relates to a detection apparatus, a detection method and a detection computer program for detecting particles. The invention relates further to a biosensor system comprising the detection apparatus.

BACKGROUND OF THE INVENTION

WO 2011/036634 A1 discloses a biosensor system comprising a biosensor cartridge with a sensor surface and first and second optical detection systems for detecting particles on the sensor surface. The first optical detection system is adapted to detect the particles by detecting intensity changes of reflected light, which has been reflected at the sensor surface, wherein the intensity changes are based on frustrated total internal reflection (FTIR). The second optical detection system is adapted to detect the particles by detecting light scattered by the particles.

JP 2008 058249 A discloses an apparatus and a method for viewing photometry. The apparatus comprises an observation system for observing an image of a sample and a photometry system that measures the strength of the light from the sample. Light from a lamp source illuminates a pinhole, and an image of the pinhole is projected on the bottom side of the sample via an optical path switching unit. Light reflected by the sample enters the switching unit again. A part of this light passes the switching unit and is detected on an imaging surface, and a further part is reflected in the switching unit and focused on a photodetector. In addition, the apparatus comprises a further light source device for illuminating the upper side of the sample for bright-field observation. Light transmitting the sample travels through the switching unit to the imaging surface.

SUMMARY OF THE INVENTION

It is an object of the present invention to provide a detection apparatus, a detection method and a detection computer program for detecting particles, which is technically less complex. It is a further object of the present invention to provide a biosensor system comprising the detection apparatus.

In a first aspect of the present invention a detection apparatus for detecting particles on or close to a particle-detection-surface is presented, wherein the detection apparatus is adapted to be operable in a first optical detection mode and in a second optical detection mode and wherein the detection apparatus comprises:
 a first light source for generating first light for illuminating the particle-detection-surface in the first optical detection mode,
 a second light source for generating second light for illuminating the particle-detection-surface in the second optical detection mode,
 a light detection system for detecting the first light and the second light after having met the particle-detection-surface,
 an optical system for modifying the first light and the second light before meeting the particle-detection-surface and/or after having met the particle-detection-surface, wherein a component of the light detection system and/or a component of the optical system is arranged to be used in the first detection mode and in the second detection mode.

Since a component of the light detection system and/or a component of the optical system is arranged to be used in the first detection mode and in the second detection mode, this component does not need to be provided twice, i.e. for being used in the first detection mode and for being used in the second detection mode. This can lead to a reduced number of components and can make the detection apparatus technically less complex.

The detection apparatus is preferentially adapted to detect particles on or close to the particle-detection-surface, whose distance to the particle-detection-surface is small enough to influence the first light and the second light when illuminating the particle-detection-surface. The detection apparatus is preferentially further adapted to use the detection of the particles on the particle-detection-surface for detecting a substance within a fluid, wherein the particles on the particle-detection-surface have been attached to, i.e. have captured, the substance and wherein the detection apparatus comprises a substance detection unit for detecting the substance based on the detected first light and/or the detected second light. The substance detection unit is preferentially adapted to determine, for instance, a concentration of the substance in the fluid based on the detected first light and/or the detected second light.

The particles are preferentially magnetic beads, particularly magnetic nanoparticles, which label a substance in a fluid, in particular, in a bodily fluid like saliva or blood. The magnetic beads are preferentially functionalized with an attaching element that can be attached to the substance being, for example, a specific analyte molecule, thereby generating substance-magnetic bead assemblies. The attaching element is, for example, an antibody, a protein, TNA, an aptamer, et cetera. The particle-detection-surface can comprise binding elements, which are adapted to bind the substance-magnetic bead assemblies, when substance molecules have been attached to the magnetic beads. The detection apparatus preferentially further comprises a magnet unit for forcing the magnetic beads onto the particle-detection-surface, in order to allow the magnetic beads that have captured the substance molecules to be bound to the binding elements on the particle-detection-surface, and to force the unbound magnetic beads away from the particle-detection-surface. The detection apparatus can therefore be regarded as being or as being a part of a magnetic biosensor, which may be adapted to perform a sandwich immunoassay.

The light detection system and the optical system are adapted such that the first light is modified by FTIR caused by the particles and that the modified first light is detected. Moreover, the light detection system and the optical system can be adapted such that the second light is scattered by the particles and that the scattered second light is detected. The detection of the particles based on FTIR is especially suited for a relatively large density of particles on the particle-detection-surface. The detection of the particles based on the scattered light is especially suited for relatively low densities of the particles on the particle-detection-surface. Thus, if the density of particles on or close to the particle-detection-surface is relatively large, the detection apparatus may be operated in the first optical detection mode for detecting the particles based on FTIR, and if the density of the particles on or close to the particle-detection-surface is relatively low, the detection apparatus may be operated in the second optical detection mode for detecting the particles based on the detection of scattered light. This allows detecting the particles reliably over a relatively large range of densities of the particles on or close to the particle-detection-surface.

The light detection system preferentially comprises a light detection surface which is arranged to be used in the first optical detection mode and in the second optical detection mode, wherein the first light is detected by a first part of the light detection surface and the second light is detected by a second part of the light detection surface. Thus, the same detection surface may be used in the first optical detection mode and in the second optical detection mode, i.e. it is not necessarily required to provide, for instance, two detectors for detecting the first light and the second light in the first optical detection mode and the second optical detection mode, respectively. This allows for a reduction of components for detecting light. The light detection surface is preferentially a light detection surface of a charge coupled device (CCD) camera or of a complementary metal-oxide-semiconductor (CMOS) camera.

It is preferred that the optical system comprises a double telecentric arrangement which is adapted to be used for modifying the first light in the first optical detection mode and for modifying the second light in the second optical detection mode. Thus, the same double telecentric arrangement may be used for the two optical detection modes, thereby reducing the number of components of the optical system. It is also preferred that the optical system comprises a permeable mirror which is adapted to be used for modifying the first light in the first optical detection mode and for modifying the second light in the second optical detection mode.

In an embodiment the light detection system comprises a light detection surface which is arranged to be used in the first optical detection mode and in the second optical detection mode, wherein the detection apparatus is adapted such that a) in the first optical detection mode the first light coming from the particle-detection-surface is directed to the permeable mirror and the first light traversing the permeable mirror is directed to the light detection surface, and b) in the second optical detection mode the light provided by the second light source element is directed to the permeable mirror, the light reflected by the permeable mirror is directed to the particle-detection-surface and the light coming from the particle-detection-surface is directed to the light detection surface. Due to the use of the permeable mirror an optical path used in the first optical detection mode may at least partly be used also in the second optical detection method, in particular, this same optical path may be used in the first and second optical detection methods in opposite directions. This allows using components of the optical system, which are arranged along this optical path, in the first optical detection method and in the second optical detection method, thereby reducing the number of components of the optical system required in the first and second optical detection modes.

In a preferred embodiment the first light source and the optical system are adapted such that in the first optical detection mode a larger area of the particle-detection-surface is illuminated and the second light source and the optical system are adapted such that in the second optical detection mode a smaller area of the particle-detection-surface is illuminated. In particular, the particle-detection-surface may comprise several detection regions, in which particles are to be detected, wherein the first light source and the optical system may be adapted such that in the first optical detection mode the larger illuminated area of the particle-detection-surface covers the several detection regions and areas between the several detection regions and wherein the second light source and the optical system may be adapted such that in the second optical detection mode only one or only several of the detection regions are illuminated, thereby illuminating the smaller area of the particle-detection-surface. Preferentially, in the second optical detection mode the different detection regions are illuminated temporarily consecutively such that light from a single detection region is detected by the light detection system at a time. This allows for a temporal multiplexing. The several detection regions may be formed by bottom surfaces of detection chambers of a cartridge.

In an embodiment the optical system is adapted such that in the second optical detection mode an illumination optical path, along which the second light travels before meeting the particle-detection-surface, and a detection optical path, along which the second light travels after having met the particle-detection-surface and before being detected by the light detection system, are provided, wherein the detection apparatus comprises a light shield like a screen arranged between the illumination optical path and the detection optical path. The light shield can reduce stray light, which may stray from the illumination optical path into the detection optical path, and can therefore be regarded as being a stray-light shield. The reduction of the stray light in the detection optical path can improve the quality of the detection of the second light which in turn can improve the quality of the detection of the particles on or close to the particle-detection-surface.

In another aspect of the present invention a biosensor system for detecting a substance within a fluid is presented, wherein the biosensor system comprises:
 a particle-detection-surface on which particles are to be detected, and
 a detection apparatus as defined in claim 11.

In a further aspect of the present invention a detection method for detecting particles on or close to a particle-detection-surface is presented, wherein the detection method is adapted to be operable in a first optical detection mode and in a second optical detection mode and wherein the detection method comprises:
 generating first light for illuminating the particle-detection-surface in the first optical detection mode by a first light source,
 generating second light for illuminating the particle-detection-surface in the second optical detection mode by a second light source,
 modifying the first light and the second light before meeting the particle-detection-surface and/or after having met the particle-detection-surface by an optical system,
 detecting the first light and the second light after having met the particle-detection-surface by a light detection system,
 wherein a component of the light detection system and/or a component of the optical system is used in the first detection mode and in the second detection mode and wherein the first light is modified by frustrated total internal reflection caused by the particles (2) and that the modified first light is detected.

In another aspect of the present invention a detection computer program for detecting particles on or close to a particle-detection-surface is presented, wherein the detection computer program comprises program code means for causing a detection apparatus as defined in claim 1 to carry out the steps of the detection method as defined in claim 13, when the computer program is run on a computer controlling the detection apparatus.

It shall be understood that the detection apparatus of claim 1, the biosensor system of claim 12, the detection method of claim 13, and the detection computer program of claim 14 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
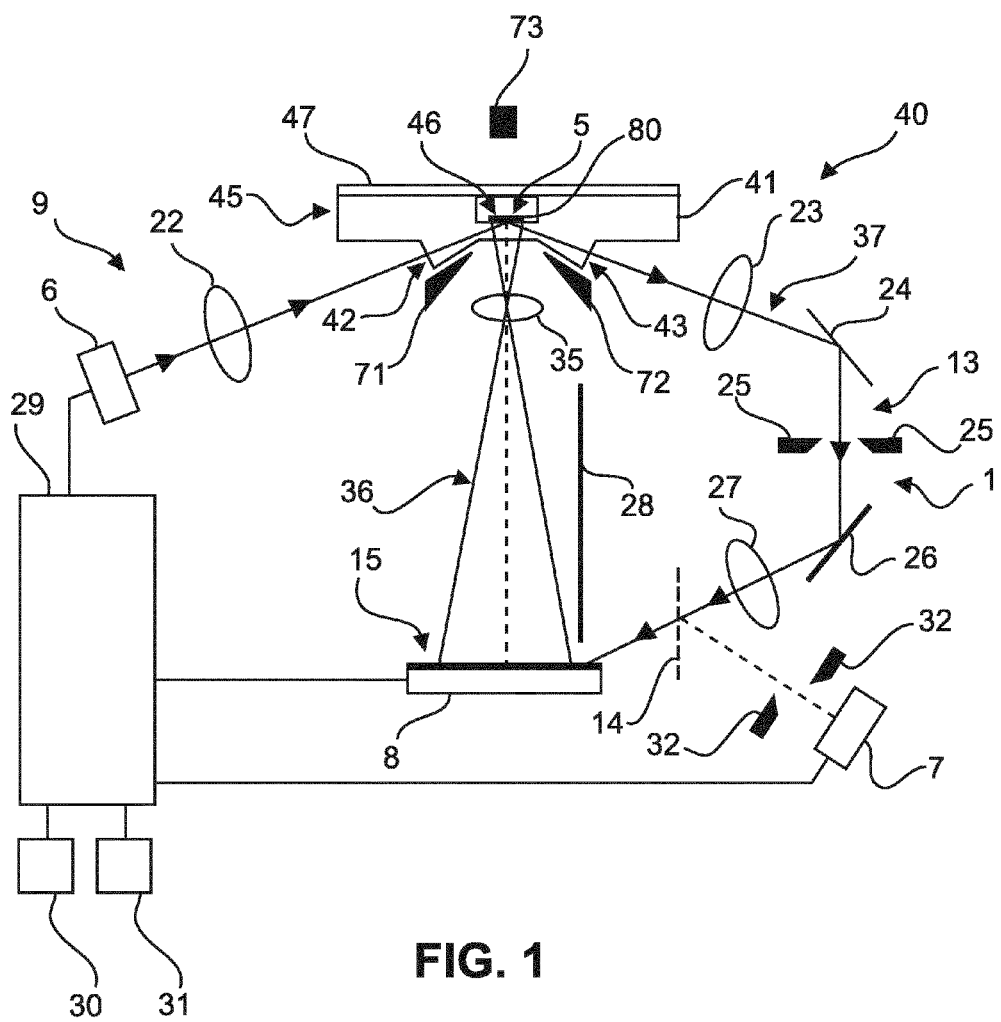
FIG. 1 shows schematically and exemplarily an embodiment of a bio sensor system in a first optical detection mode.
Figure 2:
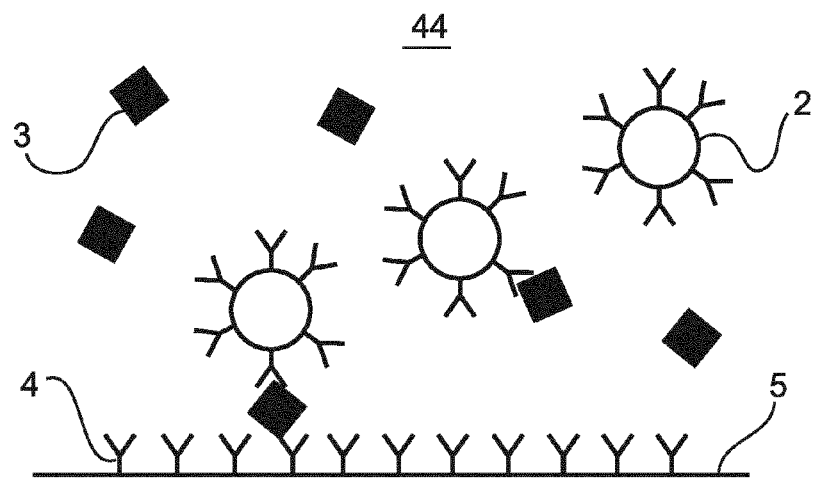
FIG. 2 illustrates schematically and exemplarily a binding of particles on the particle-detection-surface of the biosensor system.

FIG. 1 shows schematically and exemplarily an embodiment of a bio sensor system 40 comprising a detection apparatus 1 and a particle-detection-surface 5 of a biosensor cartridge 45. A binding of particles on the particle-detection-surface 5 of the biosensor cartridge 45 is schematically and exemplarily illustrated in FIG. 2.

The biosensor system 40 is adapted to detect a substance 3 within a fluid 44, which is preferentially a bodily fluid like blood or saliva, wherein the fluid has been introduced into the biosensor cartridge 45. The biosensor cartridge 45 comprises particles 2, which in this embodiment are magnetic beads functionalized for capturing the substance 3 within the fluid 44. The particle-detection-surface 5 comprises binding elements 4 for binding the magnetic beads via the substance 3, if the magnetic beads 2 have captured the substance 3.

The biosensor cartridge 45 preferentially comprises several detection chambers, of which only a single one 46 is shown in FIG. 1. Further detection chambers are arranged along a line perpendicular to the plane of FIG. 1. Each detection chamber comprises a surface with binding elements, which may be regarded as being a particles detection sub-surface of the overall particle-detection-surface including the particles detection sub-surfaces of all detection chambers or as being a detection region. Each particles detection sub-surface may comprise several binding spots, wherein each binding spot may comprise the binding elements 4.

Figure 3:
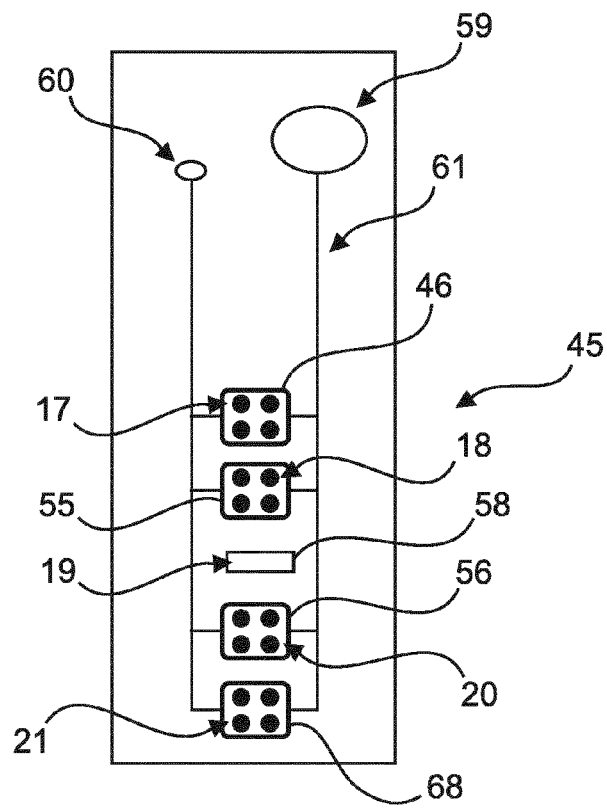
FIG. 3 shows schematically and exemplarily a biosensor cartridge of the biosensor system.

FIG. 3 schematically and exemplarily illustrates the biosensor cartridge 45 in more detail. The biosensor cartridge 45 comprises a sample deposition opening 59, through which the fluid may be introduced into the biosensor cartridge 45. The fluid is guided to the detection chambers 46, 55, 56, 68 with the detection regions 17, 18, 20, 21 comprising the binding spots via channels 61. The biosensor cartridge 45 further comprises a vent opening 60 and a true white reference (TWR) part 58 with a reference surface 19. The functionalized magnetic beads may be present in the detection chambers in dried-in form, wherein the magnetic beads may mix with the fluid, when the fluid reaches the respective detection chamber. In other embodiments the biosensor cartridge can also have another configuration, for instance, it can comprise less or more detection chambers, it may not comprise the TWR part, or the functionalized magnetic beads may be mixed with the fluid before the fluid reaches the respective detection chamber, wherein in this case the magnetic beads may be present, for instance, in a mixing chamber being arranged between the detection chambers and the sample deposition opening.

The biosensor cartridge 45 preferentially comprises a lower part 41 and an upper part 47, wherein the lower part 41 preferentially comprises the channels 61, the detection chambers 46, 55, 56, 68 and the TWR part 58 and the upper part 47 closes the detection chambers 46, 55, 56, 68, the TWR part 58 and the channels 61. The lower part 41 may be an injection molded part and the upper part 47 may be a laminate.

The detection apparatus 1 further comprises a magnet unit for forcing the magnetic beads 2 towards the particle-detection-surface 5, in order to allow the magnetic beads 2, which have captured the substance 3, to be bound by the binding elements 4, and for forcing the unbound magnetic beads 2 away from the particle-detection-surface 5. FIG. 1 schematically and exemplarily shows magnet tips 71, 72, 73 of the magnet unit, wherein the magnet tips 71, 72 on the bottom side are magnet tips of a horse shoe electromagnet and the magnet tip 73 on the top side is a magnet tip of another electromagnet. The magnet unit may be constructed, for instance, as disclosed in WO 2011/036634 A1. However, the magnet unit may also have another structure.

The detection apparatus 1 is adapted to be operable in a first optical detection mode and in a second optical detection mode. In this embodiment in the first optical detection mode the particles 2 on or close to the particle-detection-surface 5 are detected by FTIR and in the second optical detection mode the particles 2 on or close to the particle-detection-surface 5 are detected by dark field imaging of light scattered by the particles 2. In FIG. 1 a region 80 is schematically indicated, in which the particles can influence the light, wherein this region 80 is not to scale and just shown for illustrative purposes. FIG. 1 schematically and exemplarily illustrates the detection apparatus 1, when the detection apparatus 1 is operated in the first optical detection mode.

The detection apparatus 1 comprises a first light source 6 for generating first light for illuminating the particle-detection-surface 5 in the first optical detection mode. In this embodiment the first light source 6 is a light emitting diode (LED) and the first light traverses a lens 22 and is coupled into the lower part 41 of the biosensor cartridge 45 through a coupling window 42 before meeting the particle-detection-surface 5. The biosensor cartridge 45 further comprises the reference surface 19, which does not comprise binding elements and which is arranged in between the particles detection sub-surfaces or detection regions 17, 18, 20, 21. The first light source 6, the lens 22 and the lower part 41 of the biosensor cartridge 45 are preferentially adapted such that the entire particle-detection-surface including all detection regions and the reference surface is illuminated by the first light. This is schematically and exemplarily illustrated in FIG. 4.

Figure 4:
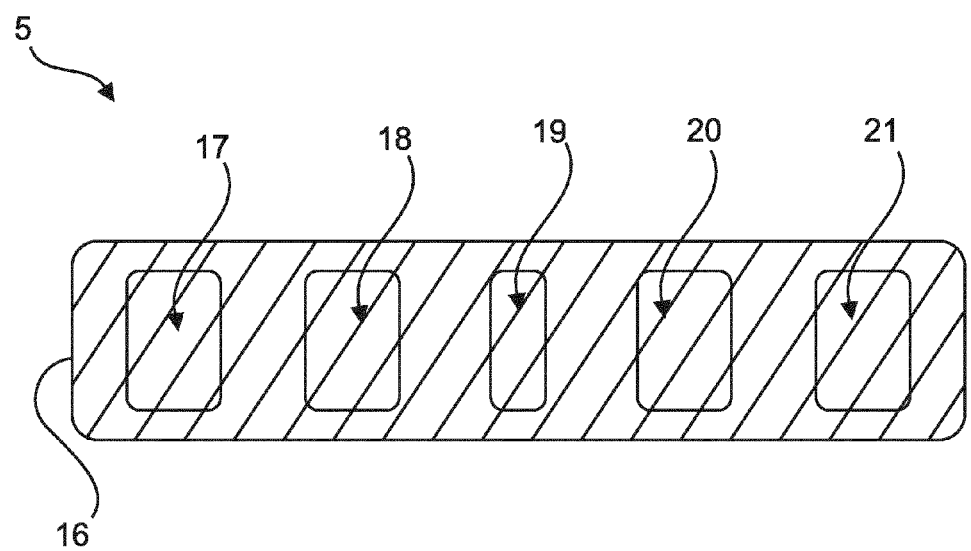
FIG. 4 illustrates schematically and exemplarily an illumination of detection regions of the bio sensor cartridge in the first optical detection mode.

FIG. 4 schematically and exemplarily illustrates an illumination of the different detection regions 17, 18, 20, 21 with the intermediate reference surface 19 in the first optical detection mode. As can be seen in this figure, an illumination area 16 generated by the first light covers all detection regions 17, 18, 20, 21 and the reference surface 19.

After having met the particle-detection-surface 5, the first light passes a double telecentric arrangement 13. The double telecentric arrangement 13 comprises a lens 23, a mirror 24, a central stop 25, a further mirror 26 and a further lens 27. The double telecentric arrangement 13 is adapted to get the same detection conditions for each detection chamber and to reduce image distortion regarding an image which is acquired by a light detection system 8 as we will describe further below. The central stop 25 between the lenses 23, 27 determines the imaging numerical aperture (NA). The mirrors 24, 26 are used to fold the optical path through the double telecentric arrangement 13 such that the first light finally meets the light detection system 8.

After having traversed the double telecentric arrangement 13, the first light traverses a permeable mirror 14 before being detected by the light detection system 8. The permeable mirror 14 is a partially reflecting mirror having, for instance, a reflectance of 90 percent and a transmittance of 10 percent.

Figure 5:
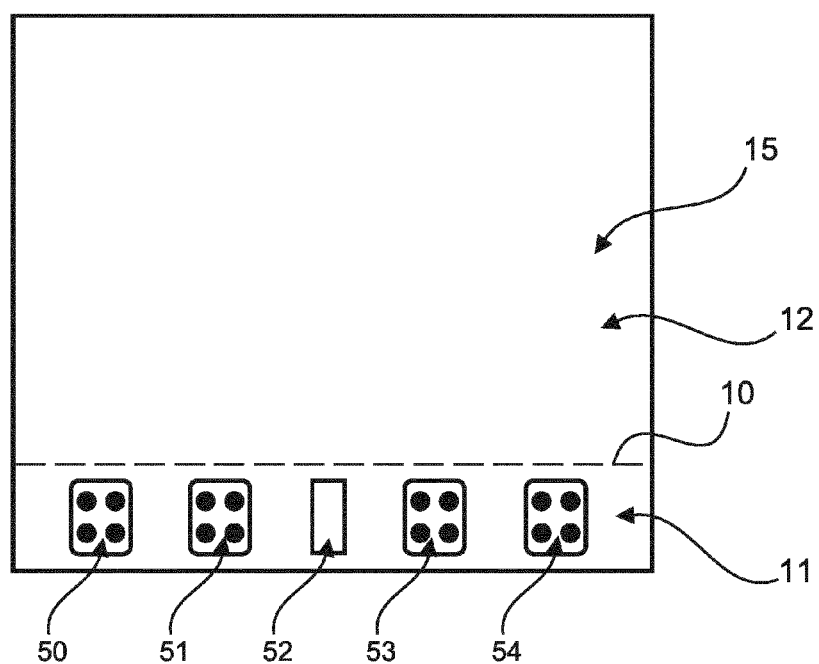
FIG. 5 shows schematically and exemplarily images on a light detection surface of the biosensor system in the first optical detection mode.

The light detection system 8 is, for instance, a CCD camera or a CMOS camera comprising a light detection surface 15, which is schematically and exemplarily illustrated in FIG. 5. The light detection surface 15 comprises a first part 11, on which the particle-detection-surface is imaged in the first optical detection mode, and a second part 12, on which the particle-detection-surface 5 is imaged in the second optical detection mode. In FIG. 5 the broken line 10 is a virtual line used for delineating the first part 11 from the second part 12.

FIG. 5 illustrates images 50, 51, 53, 54 of the bottom surfaces 17, 18, 20, 21 of the detection chambers 46, 55, 56, 68 and an image 52 of the reference surface 19 generated in the first optical detection mode on the first part 11 of the light detection surface 15. The dots within the images 50, 51, 53, 54 indicate the binding spots with the binding elements 4 on the respective bottom surface of the respective detection chamber 46, 55, 56, 68.

The images 50 . . . 54 acquired by the light detection system 8 are provided to a control unit 29 which is adapted to control the detection apparatus, in particular, the first light source 6, the light detection system 8 and a second light source 7 which will be described in more detail further below. Moreover, the control unit 29 is adapted to determine the concentration of the substance 3 within the fluid 44 based on the images 50 . . . 54 detected by the first part 11 of the light detection surface 15. The intensity of the respective part of the respective image of the respective binding spot depends on the number of particles bound at the respective binding spot, because the particles lead to an intensity reduction due to FTIR. Moreover, since the number of bound particles depends on the concentration of the substance to be detected within the fluid, the concentration of the substance within the fluid can be determined based on the intensity reduction detected by the light detection system 8.

The intensity level of the image 52 of the cartridge reference area 19 can act as a reference for the detected signals 50, 51, 53 and 54, i.e. for the respective images. Since the actual FTIR measurement is a difference measurement, comparing the actual reflected intensity levels when beads are bound to the surface, with the starting intensity level, when no beads have been attached to the surface (i.e. at the start of the assay), the accuracy of the FTIR measurement depends on the degree of constancy of the incoming intensity of the light source during the actual measurement. Any signal drift during the actual bioassay measurement, caused by temperature variations or intensity variations in the light source output, can be compensated for by realtime measurements of the intensity of the reference area 52. Since no particles can bind to the reference area 19, any variation in the reflected signal from area 52 is a direct consequence of instrumental drift or light source output variations, and can henceforth be used for correcting the signals 50, 51, 53 and 54 for these instrumental drift factors. In the end this drift compensation allows for very accurate measurements, detecting very small signal changes corresponding to low substance concentrations. For more details regarding the determination of the concentration of a substance within a fluid based on FTIR reference is made to the article "Rapid integrated biosensor for multiplexed immunoassays based on actuated magnetic nanoparticles" by D. M. Bruls et al., Lab on a Chip, volume 9, pages 3504 to 3510 (2009), which is herewith incorporated by reference.

Each detection chamber 46, 55, 56, 68 of the biosensor cartridge 45 may be sensitive for another substance within the fluid, i.e., for instance, in different detection chambers 46, 55, 56, 68 differently functionalized magnetic beads may be present, which are attached to different substances, such that the reduced intensity detected for different detection chambers 46, 55, 56, 68 is indicative of the concentration of different substances within the fluid. The different binding spots within a same detection chamber can also be used to determine redundantly several concentrations of a same substance within the fluid, wherein these concentrations can be combined for reducing possible errors. For instance, the concentrations determined for the different binding spots of a same detection chamber can be averaged.

The detection apparatus further comprises an input unit 30 like a keyboard, a computer mouse, a touch pad, et cetera and a display 31 for displaying the determined concentrations of the substances within the fluid. The input unit 30 can also be used to switch between the first optical detection mode and the second optical detection mode.

Figure 6:
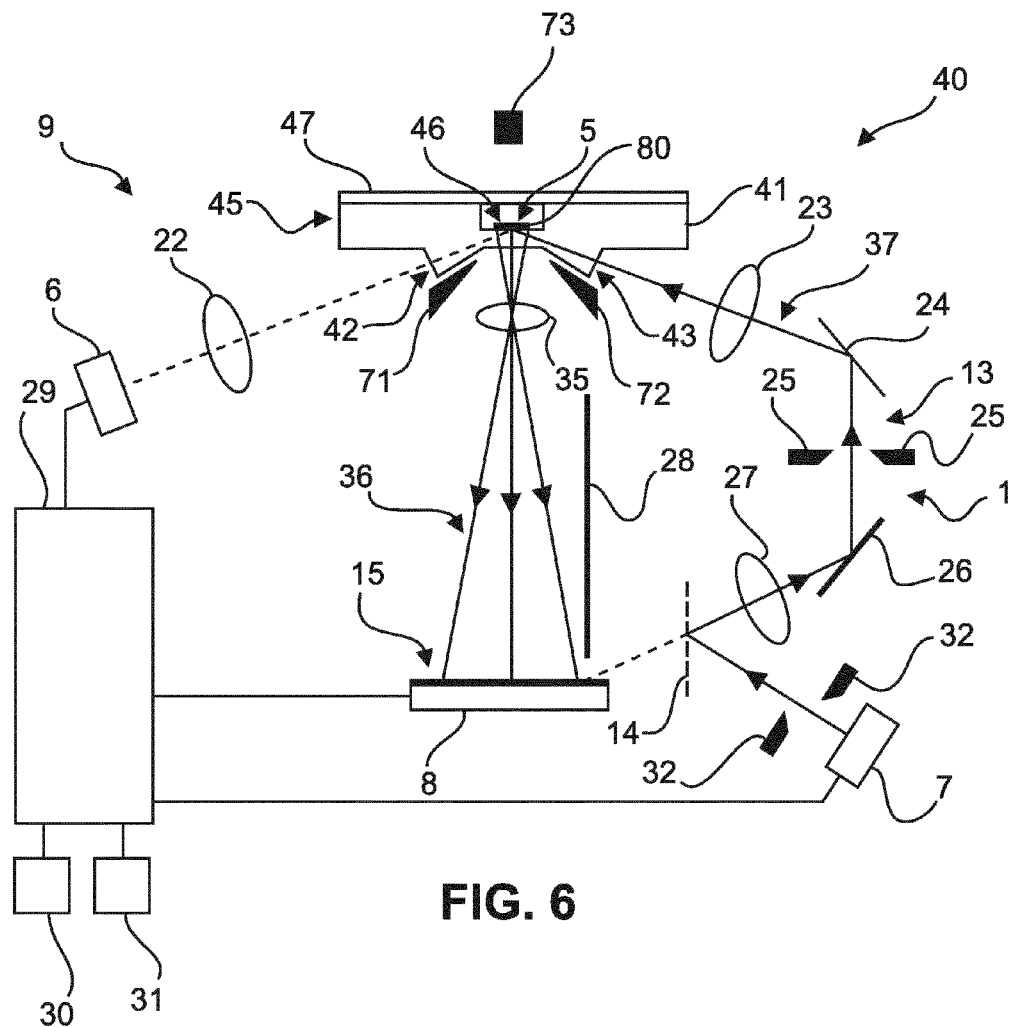
FIG. 6 shows schematically and exemplarily the biosensor system in a second optical detection mode.

FIG. 6 schematically and exemplarily illustrates the biosensor system 40 in the second optical detection mode. In the second optical detection mode the second light source 7 generates second light for illuminating the particle-detection-surface 5. In this embodiment the second light source 7 comprises four sub-light sources for illuminating the four bottom surfaces 17, 18, 20, 21 of the four detection chambers 46, 55, 56, 68 forming the particle-detection-surface 5. The second light passes a slanted diaphragm 32, is reflected by the permeable mirror 14, traverses the double telecentric arrangement 13 and is then coupled into the lower part 41 of the biosensor cartridge 45 through a coupling window 43, in order to illuminate the particle-detection-surface 5. The second light, which is scattered by the particles on or close to the particle-detection-surface 5, is projected onto the second part 12 of the light detection surface 15 of the light detection system 8 by using the lenses 35, of which only one lens is shown in FIG. 6. The lenses 35 form a one-dimensional array of lenses, which are preferentially mini-lenses, wherein the array is arranged perpendicular to the plane of FIG. 6. Moreover, the array of sub-light sources of the second light source 7 is oriented parallel to the array of detection chambers of the biosensor cartridge 45 and parallel to the array of lenses 35.

Figure 7:
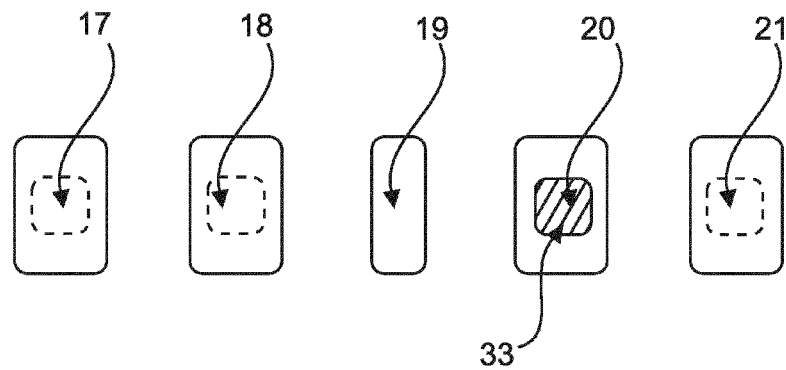
FIG. 7 illustrates schematically and exemplarily an illumination of the detection regions of the biosensor cartridge in the second optical detection mode.

The slanted diaphragm 32, the permeable mirror 14, the double telecentric arrangement 13 and the lower part 41 of the biosensor cartridge 45 are adapted such that each sub-light source of the second light source 7 illuminates a surface of a single detection chamber, i.e. a single particles detection sub-surface, only. The sub-light sources of the second light source 7 are controlled by the control unit 29 such that they are activated temporarily consecutively such that at a time only one particles detection sub-surface is illuminated and imaged onto the light detection surface 15. For instance, in the situation schematically and exemplarily illustrated in FIG. 7 only the area 33 on the particles detection sub-surface 20 is illuminated, but not the other particles detection sub-surfaces 17, 18, 21. The rectangles on the other particles detection sub-surfaces 17, 18, 21 indicate the areas, which will be illuminated at other times. Thus, in comparison to the first optical detection mode, only a relatively small area of the particle-detection-surface 5 is illuminated at a time, wherein different particles detection sub-surfaces are illuminated temporarily consecutively.

Figure 8:
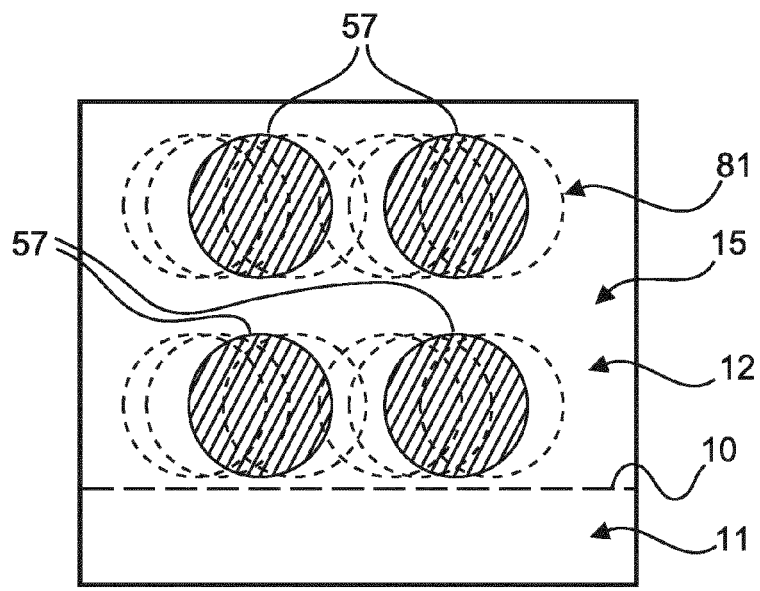
FIG. 8 shows schematically and exemplarily images on the light detection surface in the second optical detection mode.

FIG. 8 schematically and exemplarily shows the light detection surface 15 of the light detection system 8, when only the area 33 of the particles detection sub-surface 20 is illuminated. The filled circles 57 indicate the zones within which the second light scattered by the particles bound to the substrate is imaged onto the light detection surface 15, wherein the second light has been scattered by the particles bound at the four binding spots of the particles detection sub-surface 20. The other circles 81 shown in FIG. 8 indicate the positions on the light detection surface 15, onto which scattered second light will be projected, if the other sub-light sources of the second light source 7 are switched on.

Figure 9:
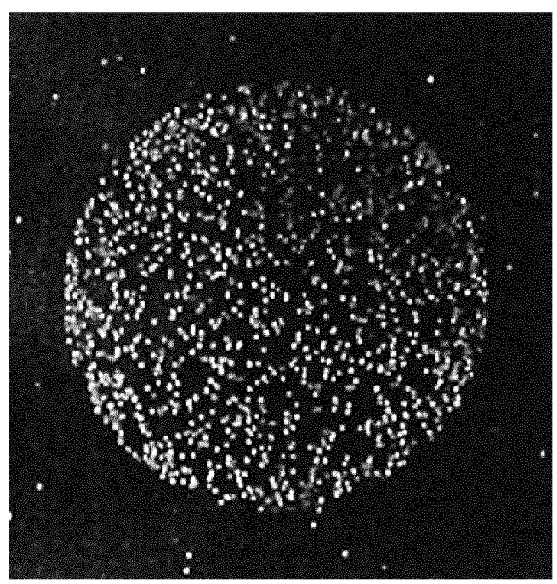
FIG. 9 shows schematically and exemplarily an image of a binding spot in the second optical detection mode.

FIG. 9 shows schematically and exemplarily one of the circles 57 in more detail. As can be seen in FIG. 9, single particles, which have scattered the second light, are identifiable such that the control unit 29 can count the number of particles within the respective binding spot. Since the number of bound particles depends on the concentration of the respective substance within the fluid, based on the determined number of particles the concentration of the respective substance within the fluid can be determined. The relation between the number of particles and the concentration of the substance can be determined in advance by a corresponding calibration procedure, wherein the number of particles within the respective binding spot is determined, while the concentration of the respective substance is known. For more details regarding the determination of the concentration of the substance within the fluid based on the scattered light reference is made to WO 2011/036634 A1, which is herewith incorporated by reference.

The lens 22, the double telecentric arrangement 13, the permeable mirror 14 and the slanted diaphragm 32 can be regarded as being components of an optical system 9 for modifying the first light and the second light before meeting the particle-detection-surface 5 and/or after having met the particle-detection-surface 5, wherein the optical path from the second light source 7 to the particle-detection-surface 5 can be regarded as being an illumination optical path 37 and the optical path from the particle-detection-surface 5 to the light detection system 8 can be regarded as being a detection optical path 36. Between the illumination optical path 37 and the detection optical path 36 a screen 28 is arranged, in order to prevent stray line from disturbing the detection of the scattered light by the light detection system 8. The screen 28 may be arranged along the virtual line 10 separating the first part 11 from the second part 12 of the light detection surface 15 of the light detection system 8.

Figure 10:
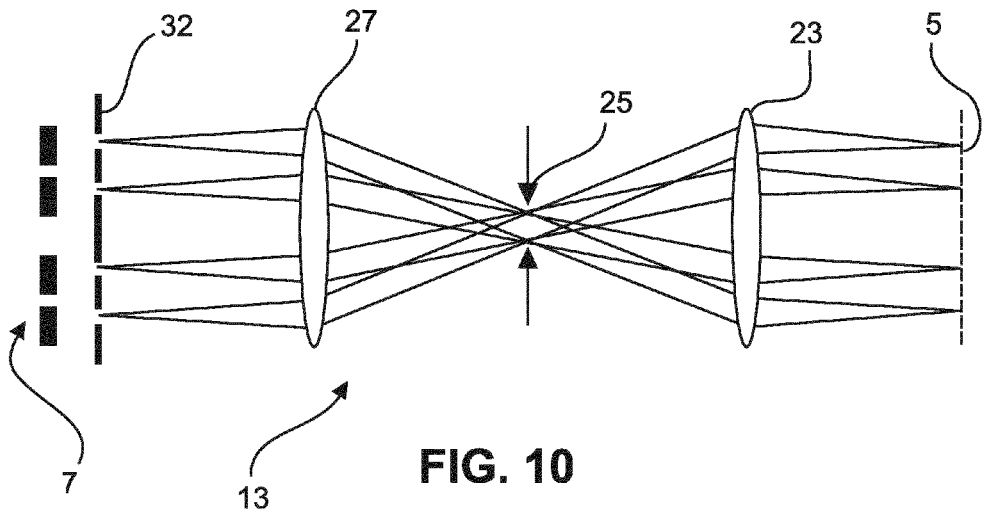
FIG. 10 shows schematically and exemplarily a top view on a double telecentric arrangement.
Figure 11:
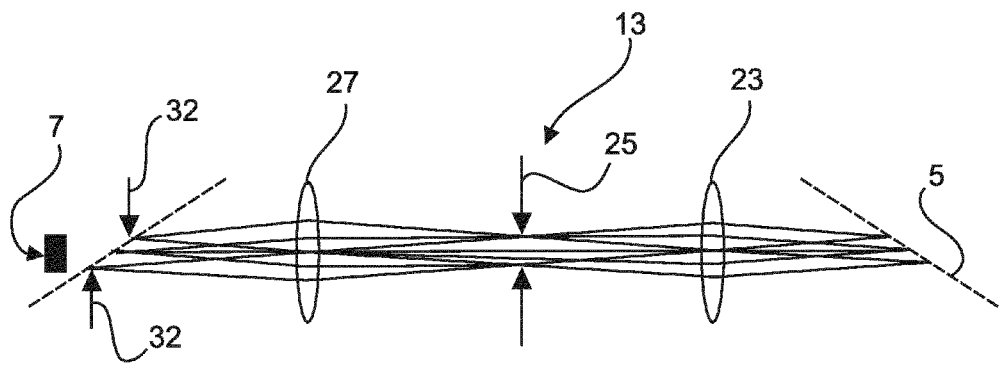
FIG. 11 shows schematically and exemplarily a side view of the double telecentric arrangement, FIG. 12 schematically and exemplarily shows a casing of the biosensor system, wherein the casing includes a detection apparatus and is adapted to receive a biosensor cartridge.

FIG. 10 shows schematically and exemplarily a top view on the double telecentric arrangement 13, after having been unfolded, and FIG. 11 schematically and exemplarily shows a side view of the unfolded double telecentric arrangement 13. As can be seen in FIG. 10, the slanted diaphragm comprises several openings, wherein each opening is associated with a corresponding sub-light source of the second light source 7.

Figure 12:
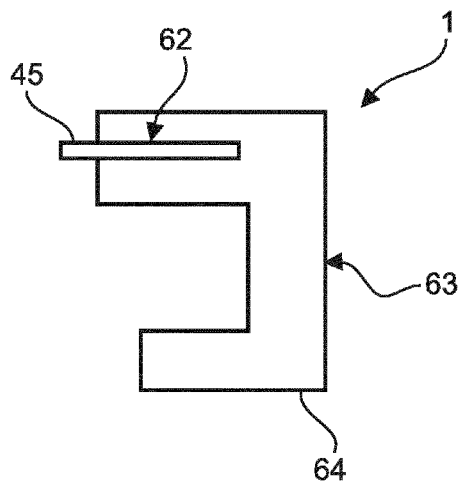

The detection apparatus 1 uses the same light detection system 8 and the same double telecentric arrangement 13 in the first optical detection mode and the second optical detection mode, wherein regarding the double telecentric arrangement 13 the same optical path is used in the first optical detection mode and the second optical detection mode, but in opposite directions. The several components of the detection apparatus 1 are preferentially arranged within a casing 64, which is schematically and exemplarily shown in FIG. 12 and which can comprise a grip part 63 for allowing a user to hold the detection apparatus 1 in the hand while detecting one or several substances within the fluid. The casing 64 comprises a receiving section 62 for receiving the biosensor cartridge 45. In other embodiments the casing 64 can have another shape.

Figure 13:
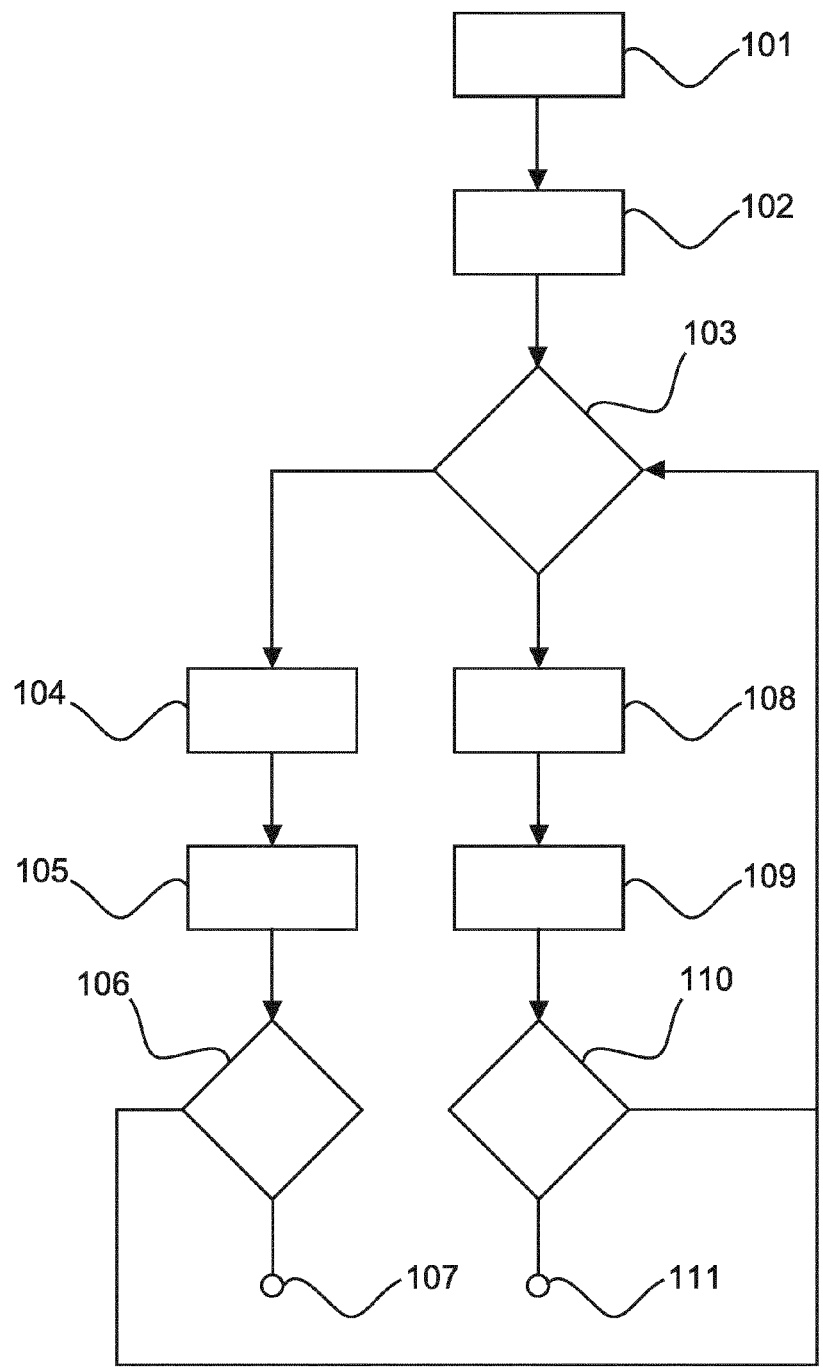
FIG. 13 shows a flowchart exemplarily illustrating an embodiment of a biosensing method, and FIGS. 14 and 15 schematically and exemplarily show images of detection regions imaged on a light detection surface.

In the following an embodiment of a biosensing method for detecting a substance within a fluid will exemplarily be described with reference to a flowchart shown in FIG. 13.

In step 101 a fluid is introduced into a biosensor cartridge and mixed with functionalized magnetic particles, which capture the substance to be detected. In step 102 the particles are forced onto the particle-detection-surface by using magnetic forces, wherein the particles, which have captured the substance, are bound to the particle-detection-surface. Then, magnetic forces are applied to the particles such that unbound particles are moved away from the particle-detection-surface. The attraction step for moving the particles towards the particle-detection-surface and the washing step for moving the unbound particles away from the particledetection-surface can be performed alternatively several times. In step 103 it can be chosen whether the detection method should be operated in the first optical detection mode or in the second optical detection mode. For instance, a user can input whether the detection method should be performed in the first optical detection mode or in the second optical detection mode. If the first optical detection mode has been chosen, the method continues with step 104. Otherwise the method continues with step 108.

In step 104 the particle-detection-surface is illuminated by the first light and the light detection system detects the first light coming from the particle-detection-surface, wherein the intensity of the detected first light is modified by FTIR. In step 105 the concentration of the substance within the fluid is determined based on the detected light intensity. In step 106 it can be decided whether the concentration of the substance within the fluid should be determined again by using, for instance, the second optical detection mode, or whether the detection method should stop in step 107. For instance, a user can indicate that the concentration should be determined again or that the biosensing method should be stopped.

If in step 103 it has been decided that the second optical detection method should be applied, in step 108 the particle-detection-surface is illuminated by the second light and the second light scattered by the particles on or close to the particle-detection-surface is detected by the light detection system. In step 109 the concentration of the substance within the fluid is determined based on the detected scattered light. In step 110 it can be decided whether the detection method should stop in step 111 or whether the detection method should continue with determining the concentration of the substance within the fluid again by using the first optical detection method or the second optical detection method. Steps 103 to 111 can be regarded as being steps of a detection method for detecting particles on or close to the particle-detection-surface.

The bio sensing method can be used for detecting a single substance within the fluid or for detecting several substances within the fluid, wherein in the latter case particle detection sub-surfaces, particularly a biosensor cartridge with different detection chambers, may be used, which bind different combinations of particles and substances.

The detection apparatus is preferentially adapted to detect specific target molecules in bodily fluids like saliva, urine, and especially blood plasma and serum. The detection apparatus and detection method can be adapted to enable selective detection of target proteins or other molecules using immunoassays based on magnetic particles. The presence of the target molecules in the sample is preferentially detected by the degree of binding of the magnetic particles, which can also be regarded as being magnetic beads, to the binding spots, which can also be regarded as being detection spot areas, which are covered with specific probes, i.e. with specific binding elements. The presence of magnetic beads bound to the particle-detection-surface is detected by optical means.

The detection apparatus may be adapted to be used in a cardiac application, wherein a blood sample is used for a quantitative detection of a number of biomarkers that are indicative of the occurrence of a myocardial infarct. The detection apparatus can be used in a point-of-care setting like an emergency room, at a bedside, in an ambulance, in a physician's office or even at home. The detection apparatus can be adapted to detect cardiac marker proteins like troponin I. Moreover, the detection apparatus may be adapted to detect myoglobin, B-type natriuretic peptide, 2,3 C-reactive protein, et cetera. A fast increase of the myoglobin level in the blood stream following a heart attack enables a rapid patient stratification. B-type natriuretic peptide is useful for the emergency diagnosis of heart failure and for the prognosis in patients with acute coronary syndromes. A simultaneous quantification of such cardiac markers can allow clinicians to diagnose coronary heart disease quickly and to accurately design a patient care strategy. A fast and reliable detection of a panel of cardiac markers will help medical professionals to differentiate between patients showing similar symptoms. Different markers are present in different diagnostically relevant concentrations and can require different assay conditions for an optimal lower limit of detection and dynamic range. For this reason the detection apparatus is preferentially adapted to perform the assays for different analytes in different detection chambers of the biosensor cartridge.

Even if the detection apparatus is used for quantifying one analyte only, multiple detection spots, i.e. binding spots, can be beneficial. The quantification accuracy can be improved by incorporating redundancy, for instance, in the form of multiple detection spot areas for the same analyte. Moreover, the dynamic range may be improved, for instance, by using multiple detection spots with varying concentrations of capture molecules, i.e. of binding elements, all specific for the same analyte. The reliability of the detection may be improved, for instance, by implementing one or more control spots as indicators that may indicate the functionality of the functionalized, i.e. antibody-coated, magnetic particles. The biosensor cartridge therefore preferentially comprises a multitude of detection spots, i.e. of binding spots, which may be arranged in different detection chambers. However, also in a single detection chamber several detection spots can be present.

The detection apparatus preferentially combines two optical detection technologies, the FTIR detection technology and the detection technology, which is based on dark field imaging of scattered light, which allows the detection of single beads and which can therefore also be regarded as being a single bead (SB) detection technology. By combining these two optical detection technologies it is possible to use the high sensitive SB detection technology for a low concentration range and to use the FTIR detection technology for larger concentration ranges, i.e. the detection apparatus is adapted to quantitatively detect biomarkers over a wide range of concentrations.

In the low concentration range the SB detection technology is a very suited "digital" technology to obtain ultimate sensitivity by detecting individual labels. A characteristic of this method, however, is that it cannot be used for high concentrations where individual beads can no longer be discriminated. It is possible to switch to global intensity detection of scattered light for that concentration range, but that approach suffers from serious calibration issues. An absolute concentration can only be derived from a scattered light intensity, if the optical illumination field intensity and the detection efficiency are well calibrated and if the biosensor cartridges are extremely reproducible. The FTIR detection technology does not suffer from this issue, because it measures a relative signal decrease during the assay, which makes it a more intrinsically normalized quantity. The lower sensitivity of the FTIR detection technique, however, makes it less suited for the low concentration range. Combining the two detection techniques offers a solution over the entire concentration range, but would in principle lead to significantly increased costs due to the relatively large amount of optical components and detection components used for the two detection techniques. The detection apparatus described above with reference to FIGS. 1 and 6 therefore reuses most of the expensive optical components and detection components. In particular, the folding of the optical path enables the use of the same light detection system for both detection techniques. In this way it is possible to have the advantages of both detection techniques, without introducing significant extra costs.

In the first optical detection mode, in which the FTIR detection technique is used, preferentially a number of detection chambers in the biosensor cartridge are globally illuminated with a limited divergence, i.e. the corresponding particles detection sub-surfaces are globally illuminated as described above with reference to FIG. 4. The reflected light is used to make an image on the light detection system of all detection areas simultaneously. To get the same detection conditions for each detection chamber and to reduce image distortion with the oblique imaging approach, it is favorable to use the double telecentric imaging arrangement. The central stop between the lenses of the double telecentric imaging arrangement limits in principle the imaging NA. In practice, however, the NA for the FTIR detection system is preferentially determined by a smaller NA of the FTIR illumination optics, so by the combination of the size of the first light source 6 and the focal length of lens 22, wherein the first light source 6 is positioned in the focal plane of the lens 22. The central stop between the lenses of the double telecentric imaging arrangement is preferentially used in the second optical detection mode to determine a larger illumination NA used in that optical detection mode. In the first optical detection mode the camera image acquired by the light detection system simultaneously shows the different detection chambers, i.e. the different particle detection sub-surfaces. Each detection chamber preferentially comprises more than one binding spot, i.e. more than one capture spot. In the embodiment described above with reference to FIGS. 1 to 9 four binding spots are present per detection chamber. However, in another embodiment also more or less binding spots can be present per chamber.

By using the FTIR detection technique essentially a decrease during the assay in the light intensity locally reflected by the binding spots is measured. This measurement is performed by taking an image before and after the assay. The measurement provides a relative signal decrease as a result of the assay. Such a relative measurement can be easily compared from analyzer to analyzer, i.e. from detection apparatus to detection apparatus, because it only depends on the linearity of the light detection system. The absolute illumination and detection powers do not need to be determined or calibrated.

In the second optical detection mode the SB detection technique is preferentially applied, wherein different detection chambers, i.e. different particles detection sub-surfaces, are temporarily consecutively illuminated. The individual detection chambers are locally illuminated with second light beams preferentially originating from separate LEDs of the second light source. This enables time-sequential illumination of one detection chamber at a time. The evanescent field of the respective illuminating light beam only interacts with the beads in direct vicinity of the respective particles detection sub-surface, wherein to each detection chamber a respective mini-objective lens 35 that images the central area of the respective detection chamber vertically down onto the second part of the light detection surface of the light detection system is assigned. In the embodiment described above with reference to FIGS. 1 to 9 the resulting image comprises four spots, which correspond to the capture or binding spots on the respective particles detection sub-surface. The images of different detection chambers can be shifted on the light detection surface due to the distance between the detection chambers. In an embodiment these shifts may be compensated by using an array of prisms. However, even without such displacement compensation the images of the detection chambers are largely overlapping on the light detection surface due to the magnification factor, wherein the magnification is chosen such that individual beads bound to the binding spots can be recognized and counted. A generally possible cross talk between the overlapping images originating from different detection chambers is avoided by the time-sequential illumination of the detection chambers.

The optical system, especially the double telecentric arrangement, is preferentially designed such that only a central part of the respective flat particles detection sub-surface is illuminated under an oblique angle. Touching the edges of the detection chambers may cause stray light, reduce the contrast and undermine the dark-field approach of the SB detection technique. Moreover, the optical system, particularly the double telecentric arrangement, is preferentially designed to keep the illumination essentially the same for each detection chamber.

Although in above described embodiments a partially transmitting mirror is used as a permeable mirror, in order to allow the detection apparatus to switch from the first optical detection mode to the second optical detection mode and vice versa, in other embodiments instead of the partially transmitting mirror other means can be used, which allow the detection apparatus to switch between the different detection modes. For instance, instead of the partially transmitting mirror an electrically, magnetically or mechanically switchable mirror may be used, which may be controllable by the control unit 29 and which preferentially is either permeable, especially substantially completely permeable, or reflecting, especially substantially completely reflecting, depending on the switching status.

Figure 14:
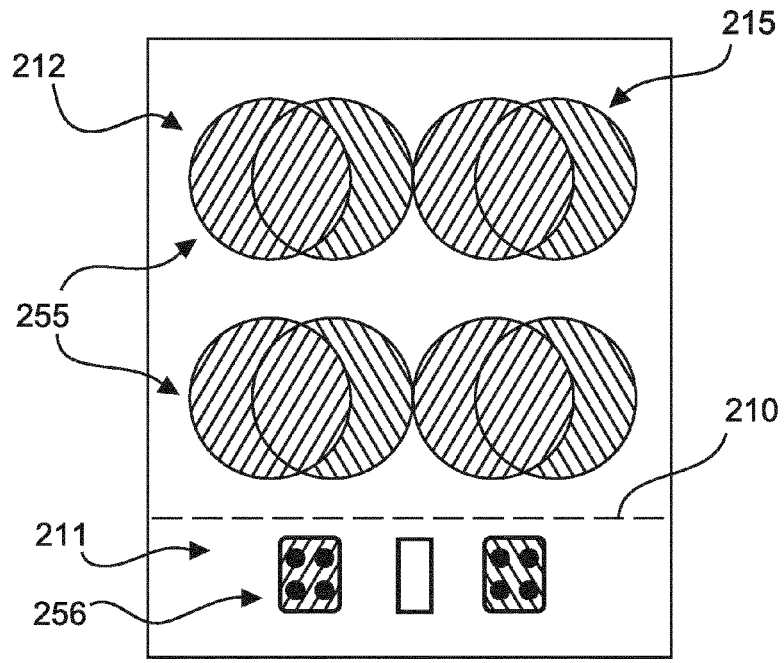
Figure 15:
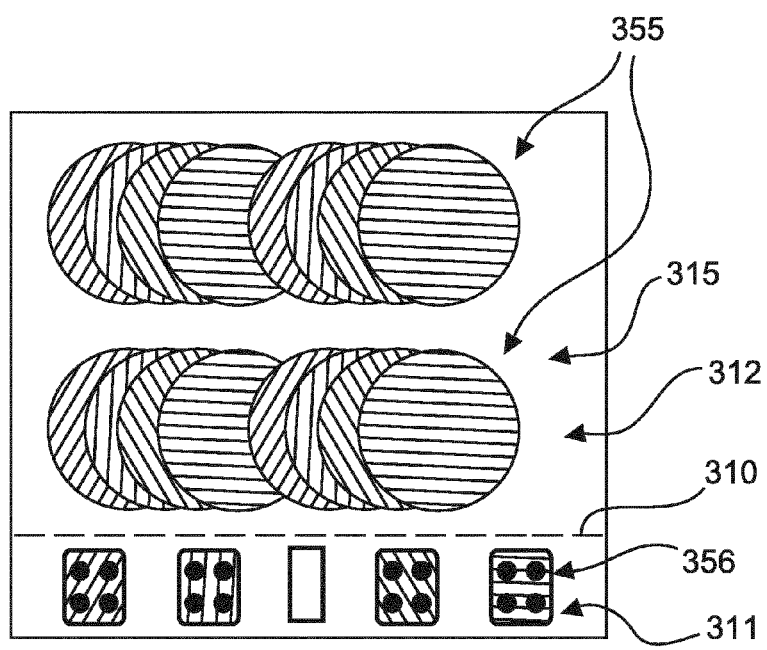

Although in FIGS. 5 and 8 a specific combination of the images of the particles detection sub-surfaces on the light detection surface is shown, in another embodiment these images, i.e. the FTIR images and the SB images, can be arranged on the light detection surface in another way, especially depending on the aspect ratio of the light detection surface and the number of detection chambers of the biosensor cartridge, which have to be multiplexed on the light detection surface. For instance, the SB images 255 and the FTIR images 256 can be arranged on the light detection surface 215 comprising a first part 211 and a second part 212 separated by a virtual line 210 as schematically and exemplarily illustrated in FIG. 14. Or, the SB images 355 and the FTIR images 356 can be arranged on the second part 312 and the first part 311 of the light detection surface 315 as schematically and exemplarily illustrated in FIG. 15, wherein in FIG. 15 reference number 310 just indicates a virtual line delineating the first part 311 from the second part 312.

The SB detection technique used in the second optical detection mode can also be regarded as being a dark-field detection technique, wherein stray light may diminish the quality of the dark-field detection technique. The detection apparatus therefore preferentially comprises the stray-light reducing screen that separates the high intensity illumination branch, i.e. the illumination optical path 37, from the low intensity SB imaging branch, i.e. the detection optical path 36.

The detection apparatus efficiently reuses expensive components like the light detection system and the double telecentric lens pair of the double telecentric arrangement. The illumination NA in the second optical detection mode, i.e. in the SB detection mode, is determined by the diaphragm in the SB illumination branch, i.e. in the illumination optical path 37. In the first optical detection mode, i.e. in the FTIR detection mode, a smaller illumination NA may be used, which is determined by the global FTIR illumination branch on the left side in FIGS. 1 and 6. The FTIR illumination divergence and thus the illumination NA used for FTIR is determined by the size of the first light source and the focal length of the lens 22 between the first light source 6 and the biosensor cartridge 45. It is therefore still possible to independently choose the NA for the FTIR illumination and for the SB illumination, wherein the NA for the FTIR illumination is preferentially lower than the NA used for SB illumination.

The partially transmitting mirror creates some loss in the SB illumination situation, i.e. in the illumination used during the second optical detection mode. The reflectance is preferentially chosen high, in order to limit the losses in the SB detection mode. In the FTIR detection mode, i.e. in the first optical detection mode, this leads to relatively high losses, but this is not a real issue, because in the first optical detection mode using the FTIR detection technique the detected intensity is relatively large, even considering these losses.

The detection apparatus can be adapted for detecting molecular targets, which often determine the concentration and/or presence of larger moieties, for example, cells, viruses, fractions of cells or fractions of viruses, tissue extract et cetera. The magnetic beads can be detected directly by the sensing method. As well, the particles can be further processed prior to detection. An example of further processing is that materials are added or that the chemical, biochemical or physical properties of the magnetic labels are modified to facilitate detection. The detection apparatus can be adapted for working together with several biochemical assay types, for example, binding/unbinding assay, sandwich assay, competition assay, displacement assay, enzymatic assay et cetera. The detection apparatus can be adapted for sensor multiplexing, i.e. the parallel use of different sensors and sensor surfaces, label multiplexing, i.e. the parallel use of different types of labels, and chamber multiplexing, i.e. the parallel use of different reaction chambers. The detection apparatus can be used as rapid, robust and easy to use point-of-care biosensor for small sample volumes. The one or several detection chambers are preferentially parts of a disposable cartridge, which is to be used with the detection apparatus, which preferentially contains one or more magnetic field generating means.

Although in above described embodiments in the first optical detection mode a first part of the light detection surface is used for detecting light and in the second optical detection mode a second part of the light detection surface is used for detecting light, wherein the first and second parts are non-overlapping, in other embodiments the first and second parts, which are illuminated in the different optical detection modes, can be overlapping, i.e. same portions of the light detection surface may be used for detecting light in the first optical detection mode and in the second optical detection mode. If this is the case, the stray-light shield is preferentially shorter, i.e. the distance between a) the end of the stray-light shield facing the light detection surface and b) the light detection surface is preferentially larger.

Although in above described embodiments in the second optical detection mode only a single detection region is illuminated at a time, in other embodiments also two or more detection regions may be simultaneously illuminated in the second optical detection mode, wherein in this case the optical system and the light detection system are adapted such that the images of the detection regions, which are simultaneously illuminated, are spatially separated on the light detection surface. Thus, in this case the optical system and the light detection system are adapted such that the images of the simultaneously illuminated detection regions do not overlap on the light detection surface.

Although in an above described embodiment the detection apparatus is adapted to allow a user select a desired optical detection mode, in another embodiment the detection apparatus may be adapted to perform both optical detection modes temporally consecutively, i.e. especially time interleaved, without necessarily requiring user interactions for selecting a certain optical detection mode. The detection apparatus may be adapted to always use both optical detection modes temporally consecutively.

Although in above described embodiments the light detection system comprises a single light detection surface of a single detector used in the first optical detection mode and in the second optical detection mode, in another embodiment the light detection system may comprises two or more light detection surfaces of two or more detectors, wherein a first detector may be used in the first optical detection mode and a second detector may be used in the second optical detection mode. In this case another component of the light detection system and/or a component of the optical system may be used in both optical detection modes.

The particles are preferentially magnetic beads being preferentially nano-particles having at least one dimension ranging between 3 nm and 10000 nm, preferably between 10 nm and 3000 nm, more preferred between 50 nm and 1000 nm.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of the concentration of the substance within the fluid based on the detected light intensities and/or the control of the detection apparatus in accordance with the detection method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a detection apparatus for detecting particles on or close to a particle-detection-surface in a first optical detection mode and in a second optical detection mode, wherein a component of a light detection system and/or a component of an optical system of the detection apparatus is arranged to be used in the first detection mode and in the second detection mode. Since a component of the light detection system and/or a component of the optical system is arranged to be used in the first detection mode and in the second detection mode, this component does not need to be provided twice, i.e. for being used in the first detection mode and for being used in the second detection mode. This can lead to a reduced number of components and can make the detection apparatus technically less complex

The invention claimed is:

1. A detection apparatus for detecting particles on or close to a particle-detection-surface, the detection apparatus being operable in a first optical detection mode and in a second optical detection mode, the detection comprising:
- a first light source for generating first light for illuminating the particle-detection-surface in the first optical detection mode;
- a second light source for generating second light for illuminating the particle-detection-surface in the second optical detection mode,
- a light detector for detecting the first light and the second light after meeting the particle-detection surface; and
- an optical system for modifying the first light and the second light at least one before meeting the particle-detection-surface, and after meeting the particle-detection-surface,
- wherein at least one of a component of the light detector and a component of the optical system is arranged to be used in the first detection mode and in the second detection mode, and
- wherein the first light is modified by frustrated total internal reflection caused by the particles and the modified first light is detected.

2. The detection apparatus of claim 1, wherein the second light is scattered by the particles and the scattered second light is detected.

3. The detection apparatus of claim 1, wherein the light detector comprises a light detection surface configured for use in the first optical detection mode and in the second optical detection mode, wherein the first light is detected by a first part of the light detection surface and the second light is detected by a second part of the light detection surface.

4. The detection apparatus of claim 1, wherein the optical system comprises a double telecentric arrangement for modifying the first light in the first optical detection mode and for modifying the second light in the second optical detection mode.

5. The detection apparatus of claim 1, wherein the optical system comprises a permeable mirror for modifying the first light in the first optical detection mode and for modifying the second light in the second optical detection mode.

6. The detection apparatus of claim 5, wherein the light detector comprises a light detection surface for use in the first optical detection mode and in the second optical detection mode, wherein:
- in the first optical detection mode, the first light coming from the particle-detection-surface is directed to the permeable mirror and the first light traversing the permeable mirror is directed to the light detection surface, and
- in the second optical detection mode, the second light provided by the second light source is directed to the permeable mirror, the second light reflected by the permeable mirror is directed to the particle-detection surface and the light coming from the particle-detection-surface is directed to the light detection surface.

7. The detection apparatus of claim 1, wherein the first light source and the optical system are configured such that in the first optical detection mode a larger area of the particle-detection-surface is illuminated, and wherein the second light source and the optical system are configured such that in the second optical detection mode a smaller area of the particle-detection-surface is illuminated.

8. The detection apparatus as defined in claim 7, wherein the particle-detection-surface comprises a plurality of detection regions, in which particles are to be detected, wherein the first light source and the optical system area configured such that in the first optical detection mode the larger illuminated area of the particle-detection surface covers the plurality of detection regions and areas between the plurality of detection regions, and wherein the second light source and the optical system are configured such that in the second optical detection mode only one detection region is illuminated or only the plurality of the detection regions are illuminated, thereby illuminating the smaller area of the particle-detection-surface.

9. The detection apparatus of claim 1, wherein a same optical path of the optical system is at least partly used, in opposite directions, in the first optical detection mode and the second optical detection mode.

10. The detection apparatus of claim 1, wherein the optical system comprises an illumination optical path, along which the second light travels before meeting the particle-detection-surface in the second optical detection mode, and a detection optical path, along which the second light travels after having met the particle-detection-surface and before being detected by the light detection system in the second optical detection mode,
- wherein the detection apparatus further comprises a light shield arranged between the illumination optical path and the detection optical path.

11. The detection apparatus of claim 1, wherein the particles on the particle-detection-surface have been attached to a substance within a fluid, and wherein the detection apparatus further comprises a controller for detecting the substance based on at least one of the detected first light and the detected second light.

12. A detection method for detecting particles bound to a particle-detection surface, the detection method comprising:
- generating first light for illuminating the particle-detection-surface in a first optical detection mode by a first light source;
- generating second light for illuminating the particle-detection-surface in a second optical detection mode by a second light source;
- modifying the first light and the second light using an optical system at least one of before illuminating the particle-detection-surface and after illuminating the particle-detection-surface, and
- detecting the first light and the second light using a light detection system after the first light and the second light have illuminated the particle-detection-surface,
- wherein at least one of a component of the light detection system and a component of the optical system is used in the first detection mode and in the second detection mode, and
- wherein the first light is modified by frustrated total internal reflection caused by the bound particles and the modified first light is detected using the light detection system.

13. A non-transitory computer readable medium storing a computer program for detecting particles bound to a particle-detection surface, when executed by a computer processor,
- first generating code causing first light to be generated by a first light source for illuminating the particle-detection-surface in a first optical detection mode;
- second generating code causing second light to be generated by a second light source for illuminating the particle-detection-surface in a second optical detection mode, wherein the first light and the second light are modified at least one of before illuminating the particle-detection-surface and after illuminating the particle-detection-surface using an optical system; and
- detecting code causing the first light and the second light to be detected by a light detection system, after having illuminated the particle-detection-surface,
- wherein at least one of a component of the light detection system and a component of the optical system is used in the first detection mode and in the second detection mode, and
- wherein the first light is modified by frustrated total internal reflection caused by the particles and the modified first light is detected.

14. The detection method of claim 12, wherein the second light is scattered by the bound particles and the scattered second light is detected using the light detection system.

15. The computer readable medium of claim 13, wherein the second light is scattered by the bound particles and the scattered second light is detected.

* * * * *